(12) United States Patent
Lange et al.

(10) Patent No.: US 10,070,902 B2
(45) Date of Patent: Sep. 11, 2018

(54) SPINAL IMPLANT SYSTEM AND METHOD

(71) Applicant: Warsaw Orthopedic, Inc, Warsaw, IN (US)

(72) Inventors: Eric C. Lange, Collierville, TN (US); Darren L. Davis, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 13 days.

(21) Appl. No.: 15/090,667

(22) Filed: Apr. 5, 2016

(65) Prior Publication Data

US 2017/0281250 A1 Oct. 5, 2017

(51) Int. Cl.
*A61B 17/70* (2006.01)
*A61B 17/88* (2006.01)
*A61B 17/56* (2006.01)

(52) U.S. Cl.
CPC ...... *A61B 17/7097* (2013.01); *A61B 17/8808* (2013.01); *A61B 2017/567* (2013.01)

(58) Field of Classification Search
CPC ............ A61B 17/7047; A61B 17/7062; A61B 17/7065; A61B 17/7067; A61B 17/7068; A61B 17/707; A61B 17/7071; A61B 17/7097; A61B 17/885; A61B 17/8852; A61B 17/8858; A61F 2/4405; A61F 2/441
See application file for complete search history.

(56) References Cited

U.S. PATENT DOCUMENTS

| | | | |
|---|---|---|---|
| 6,482,234 B1 * | 11/2002 | Weber | A61F 2/441 623/17.12 |
| 8,708,955 B2 * | 4/2014 | Tilson | A61B 17/8816 604/103.1 |
| 9,414,929 B2 * | 8/2016 | Osman | A61B 17/7097 |
| 2003/0032963 A1 * | 2/2003 | Reiss | A61B 10/025 606/90 |
| 2005/0119752 A1 * | 6/2005 | Williams | A61F 2/442 623/17.16 |
| 2005/0209629 A1 * | 9/2005 | Kerr | A61B 17/025 606/192 |
| 2007/0276496 A1 * | 11/2007 | Lange | A61B 17/7065 623/17.12 |
| 2007/0288095 A1 * | 12/2007 | Wirtel | A61F 2/441 623/17.16 |
| 2008/0077242 A1 * | 3/2008 | Reo | A61F 2/441 623/17.15 |
| 2009/0105823 A1 * | 4/2009 | Williams | A61F 2/441 623/17.16 |
| 2009/0240334 A1 * | 9/2009 | Richelsoph | A61F 2/441 623/17.16 |
| 2009/0270992 A1 * | 10/2009 | Gerber | A61F 2/441 623/17.16 |
| 2010/0222802 A1 * | 9/2010 | Gillespie, Jr. | A61B 17/0401 606/192 |
| 2012/0016371 A1 * | 1/2012 | O'Halloran | A61B 17/7097 606/94 |
| 2012/0022590 A1 * | 1/2012 | Druma | A61B 17/7065 606/249 |
| 2015/0230847 A1 * | 8/2015 | Sennett | A61B 17/8822 623/23.48 |

* cited by examiner

*Primary Examiner* — Lynnsy Summitt

(57) ABSTRACT

A spinal implant comprises a body including an inner surface that defines a cavity. The inner surface includes a baffle. The body is disposable between a contracted configuration and an in vivo expandable configuration. Systems and methods are disclosed.

15 Claims, 8 Drawing Sheets

SPINAL IMPLANT SYSTEM AND METHOD

TECHNICAL FIELD

The present disclosure generally relates to medical devices for the treatment of musculoskeletal disorders, and more particularly to a surgical system that includes a spinal implant and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes decompression, discectomy, laminectomy, laminoplasty, fusion, fixation and implantable prosthetics. For example, spinal stabilization treatments may employ implants, which may include interbody devices, plates and bone fasteners to stabilize vertebrae and facilitate healing. This disclosure describes an improvement over these prior technologies.

SUMMARY

In one embodiment, a spinal implant is provided. The spinal implant comprises a body including an inner surface that defines a cavity. The inner surface includes a baffle. The body is disposable between a contracted configuration and an in vivo expandable configuration. In some embodiments, systems, instruments and methods are provided.

BRIEF DESCRIPTION OF THE DRAWINGS

The present disclosure will become more readily apparent from the specific description accompanied by the following drawings, in which.

DETAILED DESCRIPTION

Figure 1:
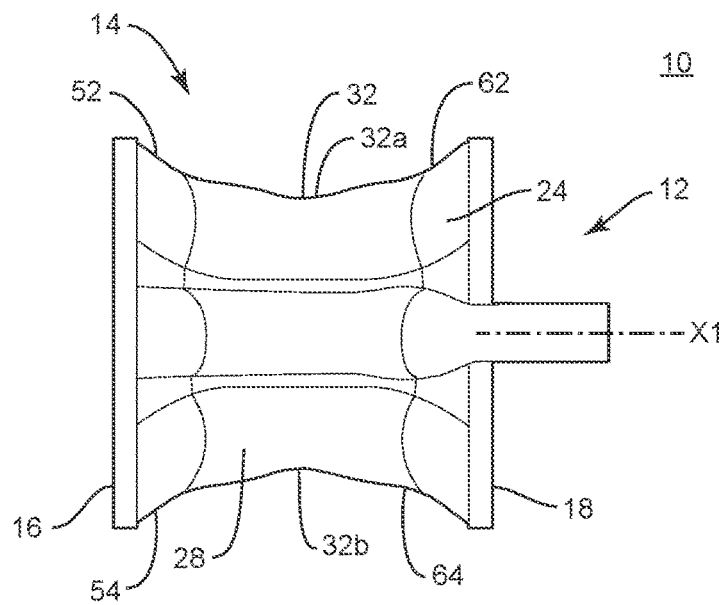
FIG. 1 is a side view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system including a spinal implant and a method for treating a spine. In some embodiments, the spinal implant includes an interbody device, an interspinous implant and/or bone fasteners. In some embodiments, the systems and methods of the present disclosure are employed with decompression, discectomy, laminectomy, laminoplasty, fusion, fixation and implantable prosthetic procedures.

In some embodiments, the surgical system includes a spinal implant having a body, such as, for example, a receptacle. In some embodiments, the receptacle includes a fabric bag. In some embodiments, the spinal implant includes baffles configured to control a final shape of the body. In some embodiments, the body is configured for disposal between a contracted configuration and an expanded configuration between spinous processes during a surgical procedure, as described herein.

In some embodiments, the spinal implant includes a body having a plurality of non-baffle zones configured to provide directional stability. In some embodiments, the spinal implant includes a body having baffles configured to limit inflation of a portion of the body. In some embodiments, the body includes an integrated fabric tube. In some embodiments, the body includes a non-permeable fabric coating.

In some embodiments, the surgical system includes a spinal implant including an injectable interspinous process device configured for injection with a flexible material. In some embodiments, the flexible material is cured in-vivo between two adjacent vertebral spinous processes. In some embodiments, utilization of the spinal implant with a surgical procedure, as described herein, will reduce patient recovery time. In some embodiments, the surgical system includes a spinal implant configured to treat degenerative disc disease, such as, for example, foraminal stenosis, facet arthropathy and/or leg and back pain. In some embodiments, the spinal implant includes, such as, for example, an interspinous process decompression device configured for disposal between the spinous processes and configured to counteract the effects of degenerative disc disease.

In some embodiments, the spinal implant is configured for disposal in a contracted configuration, such as, for example, in an unfilled orientation and an expandable configuration. In some embodiments, the spinal implant is configured for positioning between adjacent spinous processes. In some embodiments, the surgical system includes a cannula configured for disposal of the spinal implant to facilitate insertion to a surgical site. In some embodiments, the cannula is configured to provide a pathway for injecting the flexible material to inflate the spinal implant.

In some embodiments, the surgical system includes an injectable spinal implant having two non-baffle zones configured to provide directional stability. In some embodiments, the injectable spinal implant includes internal structural connections, such as, for example, baffles configured to limit cylindrical inflation. In some embodiments, the injectable spinal implant includes an integrated fabric tube. In some embodiments, the injectable spinal implant includes a non-permeable fabric coating.

In some embodiments, the surgical system includes a spinal implant having sealed ends. In some embodiments, the spinal implant includes a selected dimension between an anterior surface and a posterior surface. In some embodiments, the baffles are configured to reduce the dimension between an anterior surface and a posterior surface.

In some embodiments, the spinal implant includes a body having two non-baffle zones disposed on opposite ends of the body. In some embodiments, the non-baffle zones are configured to form flared ends to constrain the spinal implant in position between the two spinous processes after inflation. In some embodiments, the non-baffle zones are tapered to facilitate folding to constrain the spinal implant within a cannula for insertion.

In some embodiments, the spinal implant is configured to inflate to a specified size and/or shape to provide distraction in a cranial/caudal direction while limiting the inflation volume in the anterior/posterior direction. In some embodiments, the spinal implant is configured to limit a cylindrical inflation volume to resist and/or prevent pressure in the anterior/posterior direction towards a spinal canal to avoid impinging neurological structures.

In some embodiments, the spinal implant includes a straight baffle construction. In some embodiments, the spinal implant includes a cruciate and/or crisscross baffle construction. In some embodiments, the spinal implant may include multiple configurations of baffle designs to produce various shapes and facilitate engagement with different patient spinous processes anatomy.

In some embodiments, the injectable spinal implant includes a fabric bag. In some embodiments, the fabric bag is manufactured on a loom to provide for fibers to integrate seamlessly into a fabric tube. In some embodiments, the construction of the fabric bag facilitates attachment of a plastic male connector. In some embodiments, the plastic connector is configured for connection with a surgical instrument configured to inflate the spinal implant in-vivo.

In some embodiments, the fabric bag is configured to provide a controlled volume with a non-permeable outer surface. In some embodiments, the non-permeable outer surface is configured to resist and/or prevent leakage. In some embodiments, the non-permeable outer surface is configured to regulate inflation pressures required for spinal implant size, shape, and distraction force of spinous processes. In some embodiments, the non-permeable outer surface includes an anti-microbial coating and/or a silicone coating. In some embodiments, the fibers of the fabric bag can be pre-coated or the final fabric bags can be dipped and/or sprayed to fill the fabric pores.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$, polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce instrumentation and/or spinal implants, such as, for example, an interspinous implant at a surgical site within a body of a patient, which includes, for example, vertebrae. One or more of the components of spinal implant system 10 including an interspinous implant can be employed, for example, in decompression, discectomy, laminectomy, laminoplasty, fusion, fixation and implantable prosthetic procedures to treat patients suffering from a spinal disorder, as described herein, to provide stabilization and decompression. In some embodiments, one or more of the components of spinal implant system 10 are employed with a method for implanting an interspinous process spacer between two adjacent vertebrae, which includes introducing the interspinous spacer adjacent a superior spinous process and an inferior spinous process.

Spinal implant system 10 includes a spinal implant, such as, for example, an interspinous implant 12. Interspinous implant 12 includes a body 14. Body 14 extends between an end 16 and an end 18, and defines a longitudinal axis X1. Body 14 is configured for disposal between a contracted configuration (FIG. 12) to facilitate insertion with a delivery and/or insertion device or passageway, and an in vivo expandable configuration (FIG. 2), as described herein. In some embodiments, an overall geometry of body 14 may have various configurations, such as, for example, oval, oblong, triangular, rectangular, square, polygonal, irregular, uniform, non-uniform, variable and/or tapered. In some embodiments, a thickness defined by body 14 may be uniformly increasing or decreasing, or have alternate diameter dimensions along its length. In some embodiments, body 14 can have a uniform thickness/diameter.

Body 14 includes an inner surface 22 and an outer surface 24. Surfaces 22, 24 extend between ends 16, 18. Surface 22 defines a cavity 26. Cavity 26 is configured to receive the injectable material during expansion. In some embodiments, cavity 26 extends between ends 16, 18. In some embodiments, cavity 26 extends through all or a portion of body 14. In some embodiments, surfaces 22, 24 may have various surface configurations, such as, for example, rough, arcuate, undulating, porous, semi-porous, dimpled, polished and/or textured.

Body 14 includes an intermediate portion 28. Intermediate portion 28 is disposed between ends 16, 18. Intermediate portion 28 includes a baffle 30 to restrict and/or regulate the flow of the injectable material. Baffle 30 is disposed with surface 22 within intermediate portion 30. Baffle 30 and surface 22 form an expansion limit surface 32. Expansion limit surface 32 extends about intermediate portion 28. Expansion limit surface 32 includes a surface 32a configured to engage tissue, as described herein. Expansion limit surface 32 includes a surface 32b configured to engage tissue, as described herein.

Figure 3:
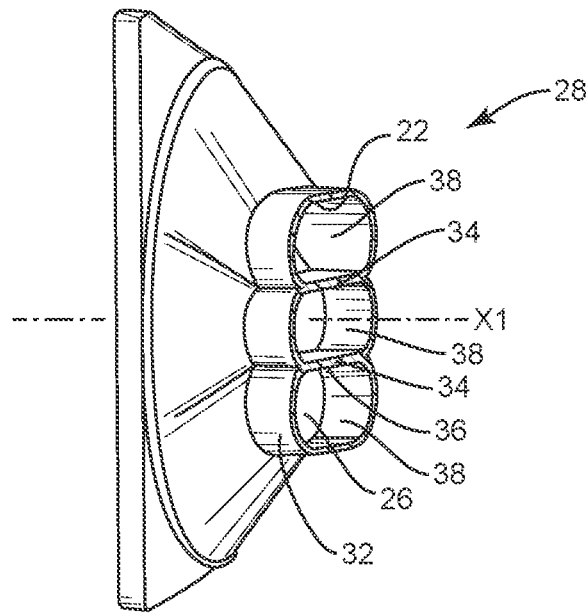
FIG. 3 is a cut-away view of the components shown in FIG. 2.

Baffle 30 includes a plurality of spaced apart walls 34 that are configured and disposed in a relative orientation to restrict and/or regulate the flow of the injectable material. Each wall 34 includes a planar surface 36. Surfaces 36 define a plurality of spaced passageways 38 selectively configured to facilitate the flow of injectable material with ends 16, 18 and portion 28 for expanding body 14. Passageways 38 are axially disposed such that passageways 38 extend parallel along axis X1, as shown in FIG. 3. In some embodiments, one or more of walls 34 and/or passageways 38 may be alternatively oriented relative to axis X1, such as, for example, transverse, perpendicular and/or other angular orientations such as acute or obtuse.

Figure 4:
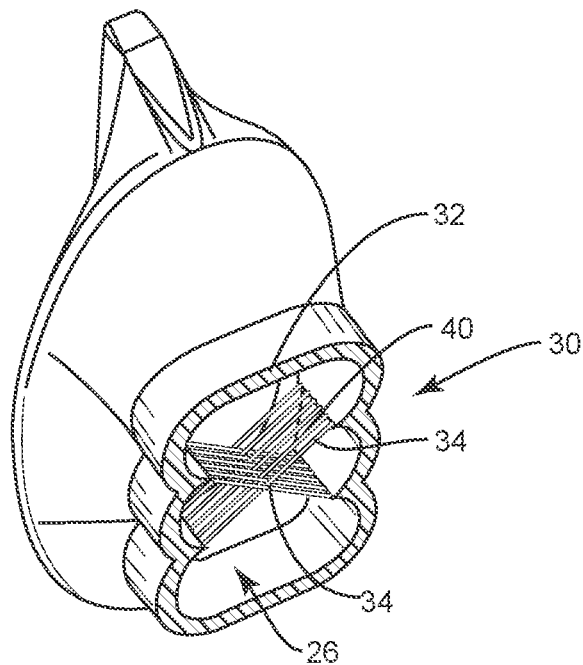
FIG. 4 is a cut-away view of components of one embodiment of a surgical system in accordance with the principles of the present disclosure.

In some embodiments, baffle 30 includes one or a plurality of walls 34 that define one or a plurality of passageways. In some embodiments, one or more of walls 34 and/or passageways 38 may be alternately configured, such as, for example, arcuate, irregular, uniform, non-uniform, variable and/or tapered. In some embodiments, one or more of surfaces 36 may include one or more openings. In some embodiments, as shown in FIG. 4, walls 34 are disposed in a cruciate configuration, such that passageways 38 extend transverse relative to axis X1. In some embodiments, walls 34 include one or plurality of threads 40, as shown in FIG. 4.

Baffle 30 is configured to restrain and/or limit expansion of body 14 adjacent a selected portion, such as, for example, intermediate portion 28 during injection of a material, as described herein. In some embodiments, as body 14 is filled with the injectable material, baffle 30 restricts and/or regulates expansion of intermediate portion 28 to resist and/or prevent expansion of expansion limit surface 32 such that body 14 is expanded to a selected configuration for disposal with tissue, as described herein. In some embodiments, body 14 can include one or more baffles disposed with all or only a portion of end 16, end 18 and/or intermediate portion 28.

Figure 2:
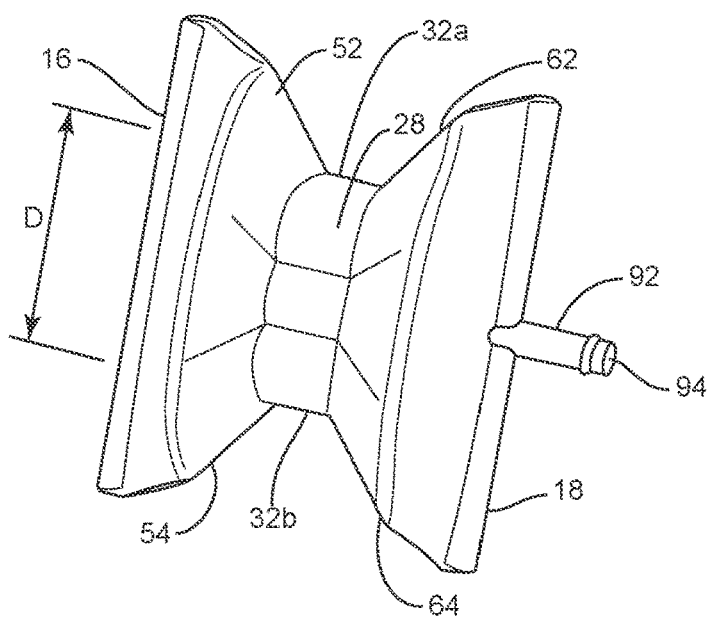
FIG. 2 is a perspective view of components of one embodiment of a surgical system in accordance with the principles of the present disclosure.

Expansion limit surface 32 is restricted with baffle 30 to reduce a dimension D of intermediate portion 28, as shown in FIG. 2. In some embodiments, baffle 30 is configured to regulate expansion of dimension D to a specific size and/or configuration to facilitate distraction in the cranial-caudal direction of a patient body. In some embodiments, baffle 30 is configured to limit expansion of dimension D in one or more directions, such as, for example, an anterior direction and a posterior direction. In some embodiments, limited expansion of intermediate portion 28 resists and/or prevents expansion of intermediate portion 28 into a spinal canal of the patient body avoiding impingement of the spinal canal.

Figure 5:
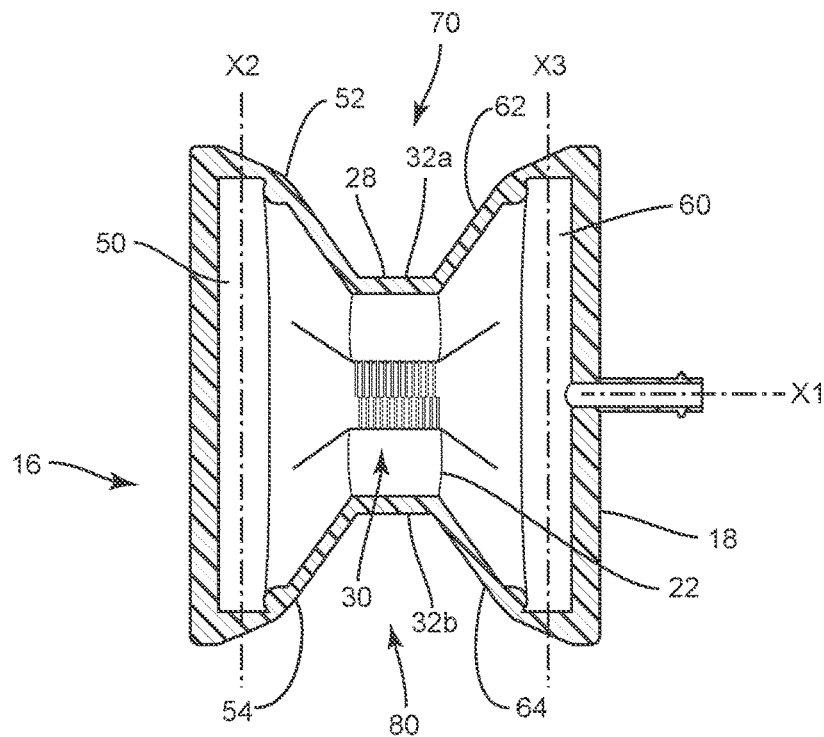
FIG. 5 is a cross section view of the components shown in FIG. 2.
Figure 6:
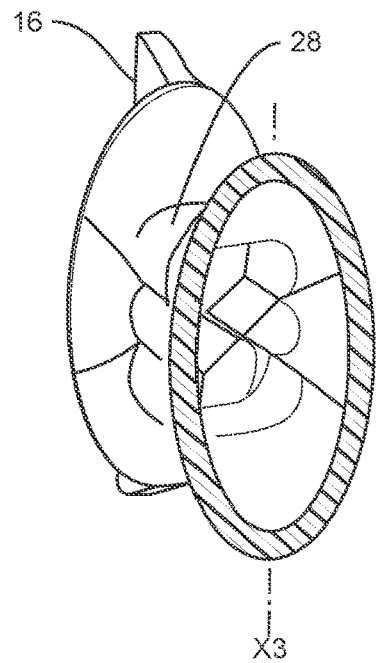
FIG. 6 is a cut-away view of the components shown in FIG. 2.

Intermediate portion 28 is tapered and/or extends in an angled orientation to end 16. End 16 includes a portion 50 having a non-baffled configuration such that portion 50 is expandable to a selected configuration, for example, to engage selected tissue. Portion 50 defines an axis X2 extending perpendicular to axis X1, as shown in FIG. 5. In some embodiments, axis X2 is disposed at alternate orientations relative to axis X1, such as, for example, transverse and/or other angular orientations such as acute or obtuse. Portion 50 includes a surface 52 and a surface 54. Surfaces 52, 54 are configured to engage tissue, as described herein.

Figure 7:
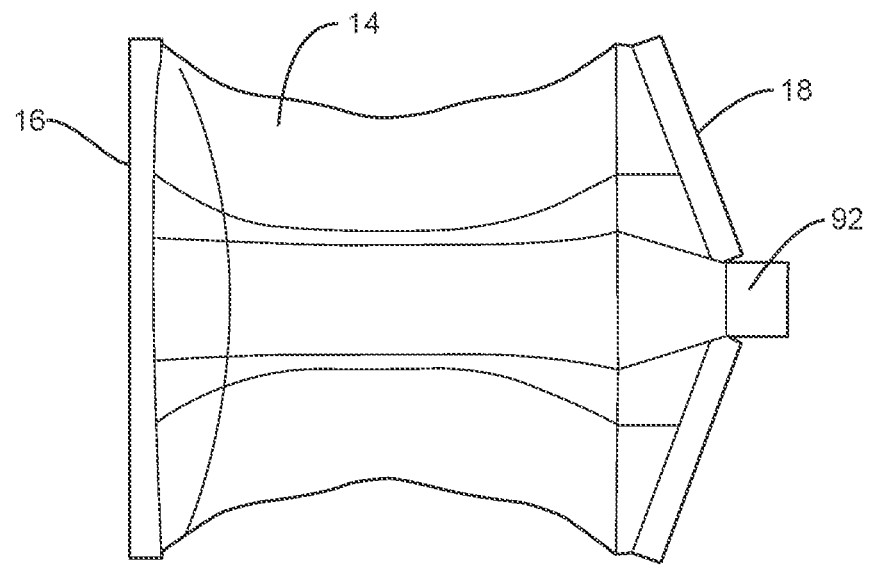
FIG. 7 is a side view of components of one embodiment of a surgical system in accordance with the principles of the present disclosure.
Figure 8:
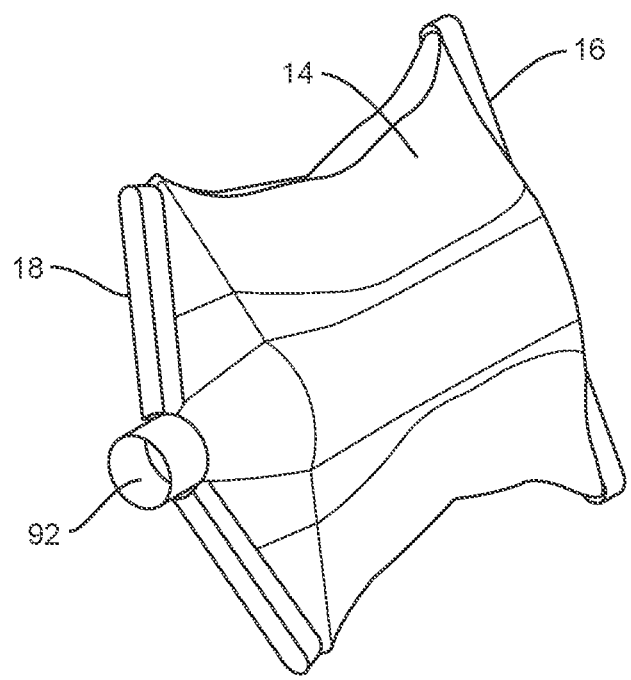
FIG. 8 is a perspective view of the components shown in FIG. 7.

In some embodiments, portion 50 is configured for expansion along axis X2 as a material is injected into body 14, as described herein, such that end 16 is expandable to the structural limits of portion 50 and/or tissue engaged therewith. Expansion of portion 50 provides directional stability to body 14 during expansion. In some embodiments, end 16 includes a flared configuration, as shown in FIGS. 7 and 8. In some embodiments, end 16 defines a straight edge, as shown in FIGS. 1 and 2.

Intermediate portion 28 is tapered and/or extends in an angled orientation to end 18. End 18 includes a portion 60 having a non-baffled configuration such that portion 60 is expandable to a selected configuration, for example, to engage selected tissue. Portion 60 defines an axis X3 extending perpendicular to axis X1, as shown in FIG. 5. In some embodiments, axis X3 is disposed at alternate orientations relative to axis X1, such as, for example, transverse and/or other angular orientations such as acute or obtuse. Portion 60 includes a surface 62 and a surface 64. Surfaces 62, 64 are configured to engage tissue, as described herein.

In some embodiments, portion 60 is configured for expansion along axis X3 as a material is injected into body 14, as described herein, such that end 18 is expandable to the structural limits of portion 60 and/or tissue engaged therewith. Expansion of portion 60 provides directional stability to body 14 during expansion. In some embodiments, end 18 includes a flared configuration, as shown in FIGS. 7 and 8. In some embodiments, end 18 defines a straight edge, as shown in FIGS. 1 and 2. In some embodiments, end 18 may have alternate configurations, such as, for example, arcuate, irregular, uniform, non-uniform and/or variable. In some embodiments, body 14 includes end 16 having a straight edge configuration and end 18 includes spaced apart, tapered sections that converge to a filling port and facilitate folding of body 14 to the contracted configuration. In some embodiments, end 16 and/or end 18 may have an arcuate configuration.

Surfaces 52, 32a and 62 are configured to define a cavity, such as, for example, a superior cavity 70. Cavity 70 is configured for disposal of vertebrae, such as, for example, a spinous process, as described herein. In some embodiments, body 14 is expanded such that surfaces 52, 32a, 62 define an arcuate profile of cavity 70 upon injection of a material with body 14. In some embodiments, the configuration and dimension of cavity 70 is adjustable via baffle 30, as described herein.

Surfaces 54, 32b and 64 are configured to define a cavity, such as, for example, an inferior cavity 80. Cavity 80 is configured for disposal of vertebrae, such as, for example, a spinous process, as described herein. In some embodiments, body 14 is expanded such that surfaces 54, 32b, 64 define an arcuate profile of cavity 80 upon injection of a material with body 14. In some embodiments, the configuration and dimension of cavity 80 is adjustable via baffle 30, as described herein.

Figure 9:
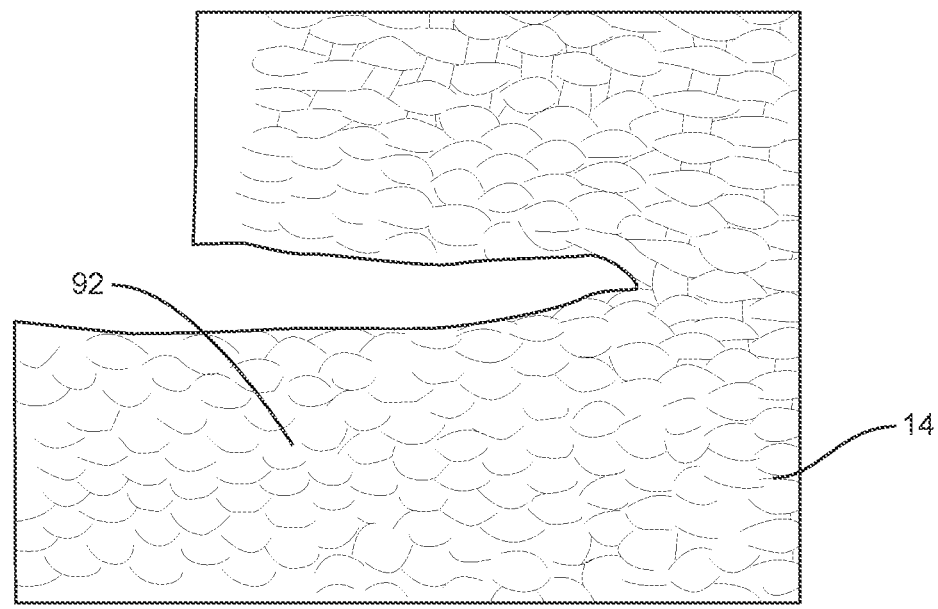
FIG. 9 is an enlarged view of material components of one embodiment of a surgical system in accordance with the principles of the present disclosure.

In some embodiments, body 14 is manufactured from a porous fabric material. In some embodiments, surface 24 is coated with a non-permeable material to coat the porous material, as shown in FIG. 9. In some embodiments, the non-permeable material is configured to prevent leakage of a material injected with body 14. In some embodiments, the non-permeable material includes an antimicrobial coating. In some embodiments, the non-permeable material includes a silicone coating. In some embodiments, surface 24 is pre-coated. In some embodiments, surface 24 is dipped in a non-permeable material. In some embodiments, surface 24 is sprayed with a non-permeable material.

Figure 10:
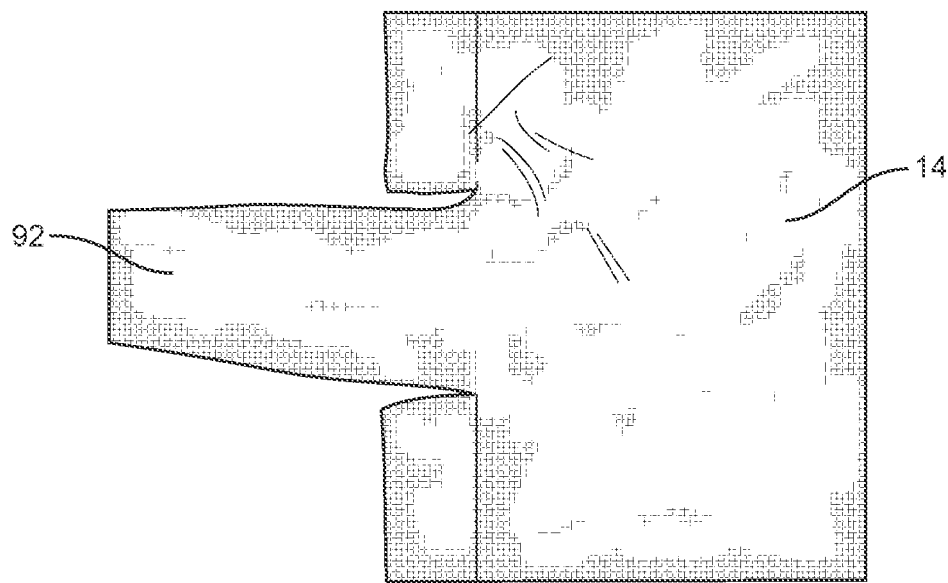
FIG. 10 is an enlarged view of material components of one embodiment of a surgical system in accordance with the principles of the present disclosure.

Body 14 includes a tubular filling port 92 disposed with end 18 and includes a plastic connector 94 configured for connection with a source of injectable material. In some embodiments, port 92 includes a fabric conduit integrated with body 14, as shown in FIG. 10. A material is injected through port 92 into body 14 for expansion of body 14 in vivo.

Body 14 is configured for disposal between a contracted configuration and an in vivo expandable configuration, as described herein. In the contracted configuration, body 14 is evacuated and ends 16, 18 and intermediate portion 28 are manipulated and/or folded into a configuration to facilitate insertion of body 14 with a delivery device, such as, for example, a cannula for disposal of interspinous implant 12 at a surgical site. Upon disposal of body 14 with a selected location at a surgical site, the cannula provides a pathway for injecting a material into cavity 26 to inflate body 14 to an expanded configuration.

A source of material is connected with port 92 and injected in vivo through the cannula into body 14 to inflate body 14. The injectable material flows through ends 16, 18 and portion 28 for expanding body 14. Baffle 30 restricts and/or regulates expansion of intermediate portion 28 to resist and/or prevent expansion of expansion limit surface 32 such that body 14 is expanded to a selected configuration for disposal with tissue, as described herein. Body 14 is expandable in vivo to a selected expanded configuration such that surfaces 52, 32*a*, 62 define cavity 70 and surfaces 54, 32*b*, 64 define cavity 80 for engagement with selected tissue surfaces, as described herein. In some embodiments, surfaces 52, 32*a*, 62 and/or surfaces 54, 32*b*, 64 are engageable with the selected tissue surfaces to resist and/or prevent undesirable movement or displacement of body 14 from the selected tissue surfaces, as described herein. In some embodiments, the injectable material is a biocompatible fluid, as described herein. In some embodiments, the injectable material includes silicone configured for injection in an initial liquid state and cured in vivo.

In assembly, operation and use, spinal implant system 10, similar to the systems and methods described herein, is employed to treat a selected section of vertebrae V, as shown in FIGS. 11-16. A medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating a spine disorder. In some embodiments, one or all of the components of spinal implant system 10 can be delivered or implanted as a pre-assembled device or can be assembled in situ. The components of spinal implant system 10 may be completely or partially revised, removed or replaced.

Figure 12:
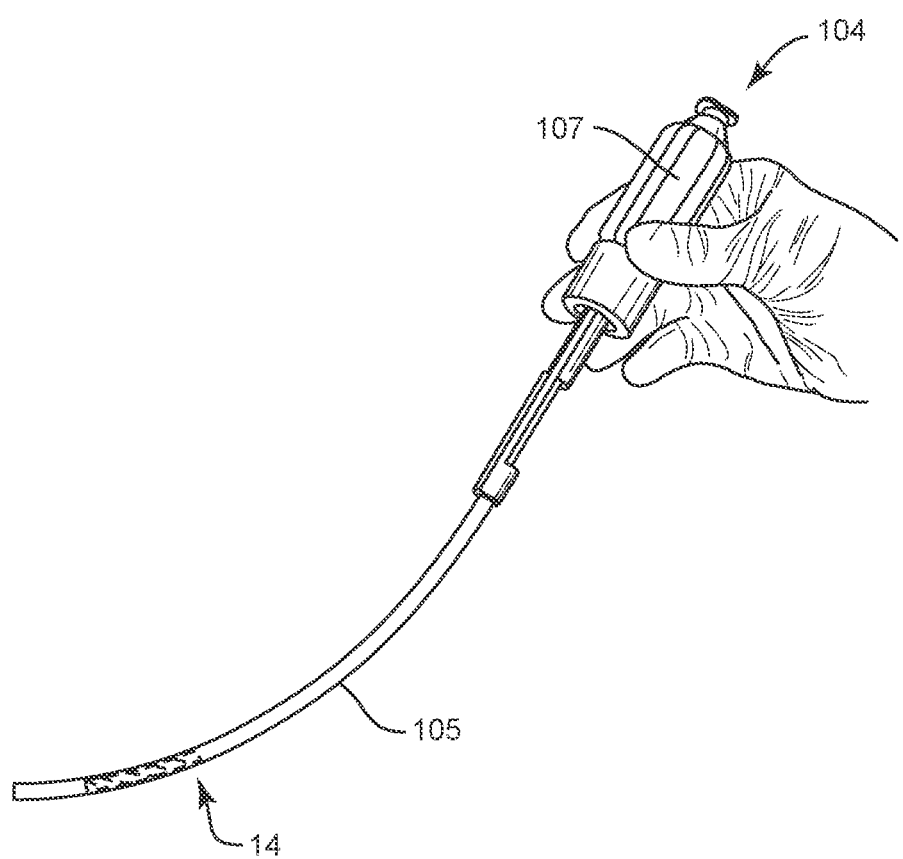
FIG. 12 is a perspective view of components of one embodiment of a surgical system in accordance with the principles of the present disclosure.

An incision is made in the body of a patient and a cutting instrument, which can include a removable inner trocar 102, as shown in FIG. 12, creates a surgical pathway for implantation of components of spinal implant system 10 with a portion of vertebrae V including spinous process SP1 and spinous process SP2. A preparation instrument (not shown) can be employed to prepare tissue surfaces of vertebrae V and a space S between spinous process SP1 and spinous process SP2, as well as for aspiration and irrigation of a surgical region.

Figure 11:
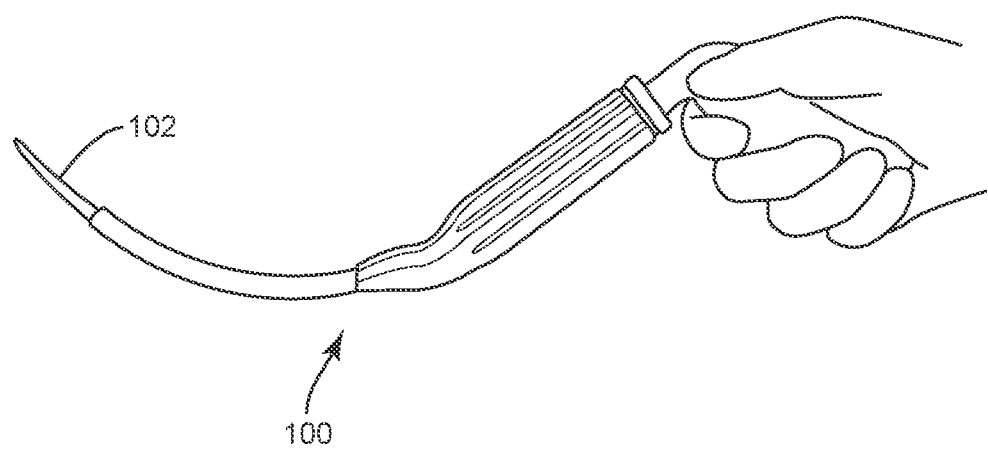
FIG. 11 is a side view of components of one embodiment of a surgical system in accordance with the principles of the present disclosure.
Figure 14:
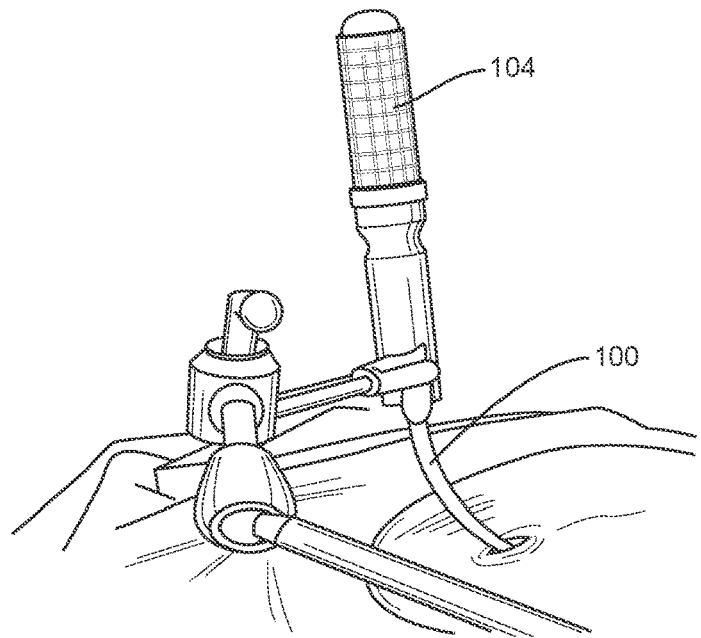
FIG. 14 is a perspective view of components of one embodiment of a surgical system in accordance with the principles of the present disclosure disposed with a patient body.

In some embodiments, a cannula 100, as shown in FIG. 11, is translated over trocar 102 and delivered via the surgical pathway for insertion adjacent the surgical site including spinous process SP1 and spinous process SP2. In some embodiments, cannula 100 includes a curved configuration to facilitate a dorsal insertion and positioning an access tip of cannula 100 between spinous process SP1 and spinous process SP2, as shown in FIG. 14. In some embodiments, trocar 102 is removed for cannula 100 to facilitate subsequent entry of an implant delivery instrument 104 through cannula 100. In some embodiments, trocar 102 includes a flexible shaft between a handle and a rigid tip to facilitate translation through a linear section of cannula 100. In some embodiments, cannula 100 and trocar 102 are positioned utilizing radiographic images. In some embodiments, cannula 100 is attached with a surgical table, as shown in FIG. 14. In some embodiments, cannula 100 includes a linear configuration. See also, the examples and disclosure of systems, surgical instruments and methods shown and described in U.S. patent application Ser. No. 15/090,694, filed Apr. 5, 2016, and published as U.S. Pat. No. 9,936,988, on Apr. 10, 2018, the entire contents of which being incorporated herein by reference.

Body 14 is evacuated and, ends 16, 18 and intermediate portion 28, are manipulated and/or folded into a contracted configuration for disposal of body 14 with a sheath 105 of delivery instrument 104 such that interspinous implant 12 is compressed and captured within delivery instrument 104 and contained within cannula 100. In some embodiments, sheath 105 is retracted via a screw mechanism (not shown) in a handle 107 of delivery instrument 104 to facilitate deployment of interspinous implant 12 at the surgical site. Interspinous implant 12 is inserted into space S and body 14 is disposed in the contracted configuration such that surface 32*a* contacts spinous process SP1 and surface 32*b* contacts spinous process SP2.

Figure 13:
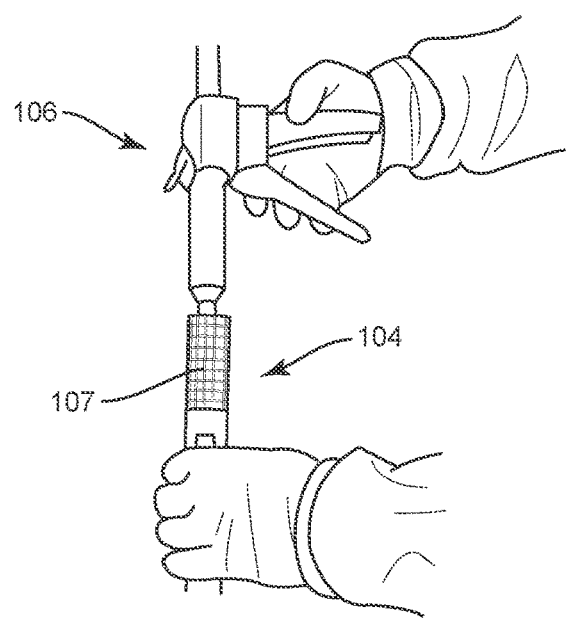
FIG. 13 is a perspective view of components of one embodiment of a surgical system in accordance with the principles of the present disclosure.

A fill tube of delivery instrument 104 is connected with connector 94. A source of injectable material, such as, for example, injector system 106 is attached with delivery instrument 104, as shown in FIGS. 13 and 14. Injector system 106 injects silicone in vivo through the fill tube of delivery instrument 104 into body 14 to inflate body 14. In some embodiments, silicone can be injected during deployment of interspinous implant 12 from delivery instrument 104. In some embodiments, silicone can be injected incrementally. In some embodiments, air trapped within delivery instrument 104 is evacuated during pre-implant injection when the silicone travels from injector system 106 through a gas/liquid check valve of delivery instrument 104 that is releasably connected with connector 94. In some embodiments, the gas/liquid check valve is releasably connected with connector 94 and/or other components of interspinous implant 12 in an in-vivo quick release configuration. In some embodiments, the quick release connection of the gas/liquid check valve with connector 94 facilitates subcutaneous release and/or detachment in-vivo of the components during employment of spinal implant system 10, for example, using a percutaneous approach. In some embodiments, the gas/liquid check valve includes a female mating element and connector 94 includes a male mating element of the in-vivo quick release configuration. In some embodiments, the gas/liquid check valve includes a male mating element and connector 94 includes a female mating element of the in-vivo quick release configuration. In some embodiments, the mating elements include detents, spring biased fingers, leer lock, clips, key/keyslot, adhesive, dovetail, friction fit and/or pressure fit. In some embodiments, the mating elements include internal and external locking features between the female and male connectors that resist and/or prevent pull forces to separate the connectors when circumferentially constrained. See also, the examples and disclosure of systems, surgical instruments, connectors, valves and methods shown and described in U.S. patent application Ser. No. 14/667,383 filed Mar. 24, 2015, and published as U.S. Pat. No. 9,968,388, on May 15, 2018, the entire contents of which being incorporated herein by reference.

Figure 15:
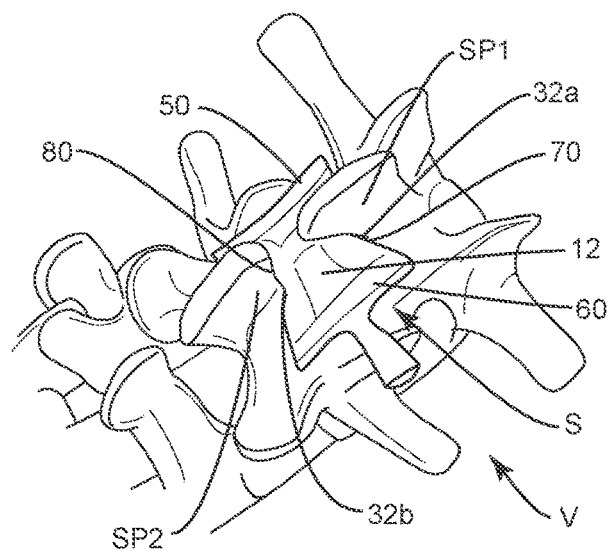
FIG. 15 is a perspective view of components of one embodiment of a surgical system in accordance with the principles of the present disclosure disposed with vertebrae.
Figure 16:
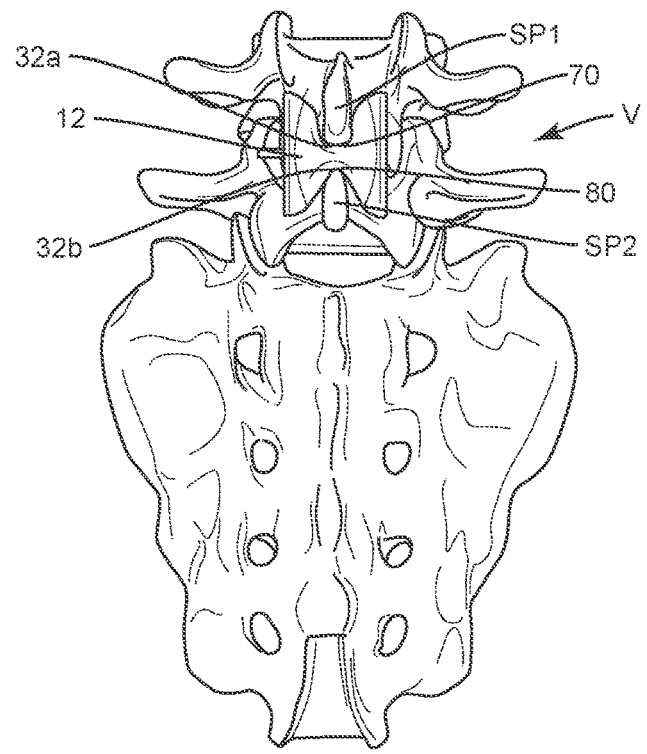
FIG. 16 is a plan view of components of one embodiment of a surgical system in accordance with the principles of the present disclosure disposed with vertebrae.

The silicone flows through ends 16, 18 and portion 28 for inflating body 14. Baffle 30 restricts and/or regulates expansion of intermediate portion 28 to resist and/or prevent expansion of expansion limit surface 32 such that body 14 is expanded to a selected configuration for disposal with spinous processes SP1, SP2. Body 14 is expandable in vivo to a selected expanded configuration, as shown in FIGS. 15 and 16, such that surfaces 52, 32*a*, 62 define cavity 70 for engagement with the selected tissue surfaces of spinous process SP1 and surfaces 54, 32*b*, 64 define cavity 80 for engagement with the selected tissue surfaces of spinous process SP2. In some embodiments, intermediate portion 28 expands in the cranial-caudal direction for distraction of spinous process SP1 and spinous process SP2. In some embodiments, baffle 30 including expansion limit surface 32 restricts expansion of dimension D of intermediate portion 28 in the anterior direction and the posterior direction to facilitate distraction of vertebrae V. The restriction of intermediate portion 28 resists and/or prevents impingement on the spinal canal of vertebrae V. In some embodiments, delivery instrument 104 is disconnected from port 92 and removed from the surgical site. The silicone disposed with body 14 in vivo is cured to harden interspinous implant 12 in the selected expanded configuration, as shown in FIGS. 15 and 16.

In some embodiments, spinal implant system 10 comprises a kit including a plurality of interbody devices, plates, bone fasteners and/or fixation elements, which may be employed with a single vertebral level or a plurality of vertebral levels. In some embodiments, the fasteners may be engaged with vertebrae in various orientations, such as, for example, series, parallel, offset, staggered and/or alternate vertebral levels. In some embodiments, the fasteners may be configured as multi-axial screws, sagittal angulation screws, pedicle screws, mono-axial screws, uni-planar screws, fixed screws, anchors, tissue penetrating screws, conventional screws, expanding screws. In some embodiments, the fasteners may be employed with wedges, anchors, buttons, clips, snaps, friction fittings, compressive fittings, expanding rivets, staples, nails, adhesives, posts, connectors, fixation plates and/or posts.

In some embodiments, spinal implant system 10 includes an agent, which may be disposed, packed, coated or layered within, on, adjacent or about the components and/or surfaces of spinal implant system 10, and/or disposed with tissue. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
a body including opposite first and second end surfaces and an intermediate portion between the end surfaces, the body including an inner surface that defines a cavity, the intermediate portion including a baffle and an inner surface defining a passageway, the baffle comprising threads each having an end that is connected to one portion of the inner surface and an opposite end that is connected to another portion of the inner surface such that the threads each extend across the passageway, the threads including a first group and a second group, the threads of the first group being interlaced with the threads of the second group,
the body being disposable between a contracted configuration and an in vivo expandable configuration.

2. A spinal implant as recited in claim 1, wherein the baffle comprises an expansion limit surface disposed adjacent a selected portion of the body.

3. A spinal implant as recited in claim 1, wherein the baffle comprises an expansion limit surface disposed adjacent an intermediate portion of the body.

4. A spinal implant as recited in claim 1, wherein the baffle includes a cruciate configuration.

5. A spinal implant as recited in claim 1, wherein the threads of the first group each extend parallel to one another, the threads of the second group each extend parallel to one another, the threads of the first group extending transverse to the threads of the second group.

6. A spinal implant as recited in claim 1, wherein the body includes a first non-baffle end portion that includes the first end surface and a second non-baffle end portion that includes the second end surface.

7. A spinal implant as recited in claim 1, wherein the body includes a first flared end portion that includes the first end surface and a second flared end portion that includes the second end surface.

8. A spinal implant as recited in claim 1, wherein the body includes a tubular fabric filling port.

9. A spinal implant as recited in claim 1, wherein the body includes a non-permeable outer surface.

10. A spinal implant as recited in claim 1, wherein the body includes a non-permeable fabric coating.

11. A spinal implant as recited in claim 1, wherein the body includes an anti-microbial coating.

12. A spinal implant comprising:
a body including opposite first and second planar end surfaces and an intermediate portion between the end surfaces, the body including an inner surface that defines a cavity, the body further including a first vertebral engaging surface and a second vertebral engaging surface, the intermediate portion including a baffle and an inner surface defining a passageway, the baffle comprising an expansion limit of the intermediate portion, the baffle comprising threads each having an end that is connected to one portion of the inner surface and an opposite end that is connected to another portion of the inner surface such that the threads each extend across the passageway, the threads including a first group and a second group, the threads of the first group being interlaced with the threads of the second group; and
a filling port extending from the body and communicating with the cavity,
the body being disposable between a contracted configuration and an in vivo expandable configuration.

13. A spinal implant as recited in claim 12, wherein the body includes a first non-baffle end portion that includes the first end surface and a second non-baffle end portion that includes the second end surface.

14. A spinal implant system comprising:
a spinal implant including a body including opposite first and second end surfaces and an intermediate portion between the end surfaces, the body including an inner surface that defines a cavity, the intermediate portion including a baffle and an inner surface defining a passageway, the baffle comprising an expansion limit of the intermediate portion, the baffle comprising threads each having an end that is connected to one portion of the inner surface and an opposite end that is connected to another portion of the inner surface such that the threads each extend across the passageway, the threads including a first group and a second group, the threads of the first group being interlaced with the threads of the second group;
a filling port extending from the body and communicating with the cavity; and
an in vivo curable material introduced via the port into the cavity to expand the body.

15. A spinal implant system as recited in claim 14, wherein the body includes a non-permeable fabric coating.

* * * * *